US011825867B2

(12) United States Patent
Markosyan

(10) Patent No.: US 11,825,867 B2
(45) Date of Patent: Nov. 28, 2023

(54) STEVIA COMPOSITION

(71) Applicant: PureCircle Sdn Bhd, Kuala Lumpur (MY)

(72) Inventor: Avetik Markosyan, Yerevan (AM)

(73) Assignee: PureCircle Sdn Bhd, Kuala Lumpur (MY)

( * ) Notice: Subject to any disclaimer, the term of this patent is extended or adjusted under 35 U.S.C. 154(b) by 0 days.

(21) Appl. No.: 15/882,532

(22) Filed: Jan. 29, 2018

(65) Prior Publication Data

US 2018/0146700 A1 May 31, 2018

Related U.S. Application Data

(62) Division of application No. 13/885,591, filed as application No. PCT/US2011/047499 on Aug. 11, 2011, now Pat. No. 9,877,501.

(60) Provisional application No. 61/492,897, filed on Jun. 3, 2011.

(51) Int. Cl.
*A23L 2/60* (2006.01)
*A23L 27/00* (2016.01)
*A23L 27/30* (2016.01)
*C07H 15/256* (2006.01)

(52) U.S. Cl.
CPC .............. *A23L 2/60* (2013.01); *A23L 27/33* (2016.08); *A23L 27/36* (2016.08); *A23L 27/88* (2016.08); *C07H 15/256* (2013.01)

(58) Field of Classification Search
CPC ............ A23L 2/60; A23L 27/88; A23L 27/33
See application file for complete search history.

(56) References Cited

U.S. PATENT DOCUMENTS

| | | | |
|---|---|---|---|
| 3,723,410 A | 3/1973 | Persinos | |
| 4,082,858 A | 4/1978 | Morita et al. | |
| 4,171,430 A | 10/1979 | Matsushita et al. | |
| 4,219,571 A | 8/1980 | Miyake | |
| 4,353,889 A | 10/1982 | DuBois | |
| 4,361,697 A | 11/1982 | Dobberstein et al. | |
| 4,404,367 A | 9/1983 | Stephenson et al. | |
| 4,454,290 A | 6/1984 | Dubois | |
| 4,590,160 A | 5/1986 | Nishihaski et al. | |
| 4,599,403 A | 7/1986 | Kumar | |
| 4,612,942 A | 9/1986 | Dobberstein et al. | |
| 4,657,638 A | 4/1987 | le Grand et al. | |
| 4,892,938 A | 1/1990 | Giovanetto | |
| 4,917,916 A | 4/1990 | Hirao et al. | |
| 5,112,610 A | 5/1992 | Kienle | |
| 5,576,042 A | 11/1996 | Fuisz | |
| 5,779,805 A | 7/1998 | Morano | |
| 5,962,678 A | 10/1999 | Payzant et al. | |
| 5,972,120 A | 10/1999 | Kutowy et al. | |
| 6,031,157 A | 2/2000 | Morita et al. | |
| 6,080,561 A | 6/2000 | Morita et al. | |
| 6,204,377 B1 | 3/2001 | Nishimoto et al. | |
| 6,228,996 B1 | 5/2001 | Zhou et al. | |
| 6,706,304 B1 | 3/2004 | Ishida et al. | |
| 7,807,206 B2 | 10/2010 | Magomet et al. | |
| 7,838,044 B2 | 11/2010 | Abelvan et al. | |
| 7,862,845 B2 | 1/2011 | Magomet et al. | |
| 8,257,948 B1 | 9/2012 | Markosyan | |
| 2002/0132320 A1 | 9/2002 | Wang et al. | |
| 2003/0161876 A1 | 8/2003 | Hansson et al. | |
| 2003/0236399 A1 | 12/2003 | Zheng et al. | |
| 2006/0083838 A1 | 4/2006 | Jackson et al. | |
| 2006/0134292 A1 | 6/2006 | Abelyan et al. | |
| 2006/0142555 A1 | 6/2006 | Jonnala et al. | |
| 2007/0082102 A1 | 4/2007 | Magomet et al. | |
| 2007/0082103 A1 | 4/2007 | Magomet et al. | |
| 2007/0116800 A1 | 5/2007 | Prakash | |
| 2007/0116819 A1 | 5/2007 | Prakash | |
| 2007/0116820 A1 | 5/2007 | Prakash | |
| 2007/0116821 A1 | 5/2007 | Prakash | |
| 2007/0116822 A1 | 5/2007 | Prakash | |
| 2007/0116823 A1 | 5/2007 | Prakash | |
| 2007/0116824 A1 | 5/2007 | Prakash | |
| 2007/0116825 A1 | 5/2007 | Prakash | |
| 2007/0116826 A1 | 5/2007 | Prakash | |
| 2007/0116827 A1 | 5/2007 | Prakash | |
| 2007/0116828 A1* | 5/2007 | Prakash | ............... A23L 1/2364 426/548 |
| 2007/0116829 A1 | 5/2007 | Prakash | |
| 2007/0116830 A1* | 5/2007 | Prakash | ............ A23C 19/0925 426/548 |
| 2007/0116831 A1 | 5/2007 | Prakash | |
| 2007/0116832 A1 | 5/2007 | Prakash | |

(Continued)

FOREIGN PATENT DOCUMENTS

| | | |
|---|---|---|
| BR | P10701736 | 7/2008 |
| CN | 1049666 | 3/1991 |

(Continued)

OTHER PUBLICATIONS

A-Glucosyltransferase Treated Stevia, Japan's Specifications and Standards for Food Additives, VIII edition, 2009, p. 257.
Ahmed, et al., "Use of p-Bromophenacyl Bromide to Enhance Ultraviolet Detection of Water-Soluble Organic Acids (Steviolbioside and Rebaudioside B) in High-Performance Liquid Chromatographic Analysis", Journal of Chromatography, vol. 192, 1980, 387-393.
Chang, S.S. et al., "Stability Studies of Stevioside and Rebaudioside A in Carbonated Beverages", Journal of Agricultural and Food Chemistry, vol. 31, 1983, 409-412.
Chen, et al., "Enrichment and separation of rebaudioside A from stevia glycosides by a novel adsorbent with pyridyl group", Science in China, vol. 42, No. 3 1999, 277-282.
Chen, et al., "Selectivity of polymer adsorbent in adsorptive separations of stevia diterpene glycisides", Science in China, vol. 41, No. 4 1998, 436-441.
Chen, et al., "Studies on the adsorptive selectivity of the polar resin with carbonyl group on rebaudioside A", Acta Polymeric Scnica, No. 4 1999, 398-403.

(Continued)

*Primary Examiner* — Nikki H. Dees
(74) *Attorney, Agent, or Firm* — Rachel Casey

(57) ABSTRACT

Stevia compositions are prepared from steviol glycosides of *Stevia rebaudiana* Bertoni. The compositions are able to provide a superior taste profile and can be used as sweetness enhancers, flavor enhancers and sweeteners in foods, beverages, cosmetics and pharmaceuticals.

7 Claims, 3 Drawing Sheets

(56) References Cited

U.S. PATENT DOCUMENTS

| | | |
|---|---|---|
| 2007/0116833 A1 | 5/2007 | Prakash |
| 2007/0116834 A1 | 5/2007 | Prakash |
| 2007/0116835 A1 | 5/2007 | Prakash |
| 2007/0116836 A1 | 5/2007 | Prakash |
| 2007/0116837 A1 | 5/2007 | Prakash |
| 2007/0116838 A1 | 5/2007 | Prakash |
| 2007/0116839 A1 | 5/2007 | Prakash |
| 2007/0116840 A1 | 5/2007 | Prakash |
| 2007/0116841 A1 | 5/2007 | Prakash |
| 2007/0128311 A1 | 6/2007 | Prakash |
| 2007/0134390 A1 | 6/2007 | Prakash |
| 2007/0134391 A1 | 6/2007 | Prakash |
| 2007/0224321 A1 | 9/2007 | Prakash |
| 2007/0292582 A1 | 12/2007 | Prakash et al. |
| 2008/0064063 A1 | 3/2008 | Brandle et al. |
| 2008/0102497 A1 | 5/2008 | Wong et al. |
| 2008/0107775 A1 | 5/2008 | Prakash |
| 2008/0107776 A1 | 5/2008 | Prakash |
| 2008/0107787 A1 | 5/2008 | Prakash |
| 2008/0108710 A1 | 5/2008 | Prakash |
| 2008/0111269 A1 | 5/2008 | Politi et al. |
| 2008/0226797 A1 | 9/2008 | Lee et al. |
| 2008/0226802 A1* | 9/2008 | Lee .............. A23L 2/02 426/594 |
| 2008/0292764 A1 | 11/2008 | Prakash et al. |
| 2008/0292765 A1 | 11/2008 | Prakash |
| 2008/0292775 A1 | 11/2008 | Prakash |
| 2008/0300402 A1 | 12/2008 | Yang et al. |
| 2009/0017185 A1* | 1/2009 | Catani .............. A23F 3/163 426/658 |
| 2009/0053378 A1 | 2/2009 | Prakash |
| 2009/0074935 A1 | 3/2009 | Lee |
| 2009/0142817 A1 | 6/2009 | Norman et al. |
| 2009/0226590 A1 | 9/2009 | Epuache et al. |
| 2010/0055752 A1 | 3/2010 | Kumar |
| 2010/0056472 A1 | 3/2010 | Duan et al. |
| 2010/0099857 A1 | 4/2010 | Evans et al. |
| 2010/0120710 A1 | 5/2010 | Watanabe et al. |
| 2010/0189861 A1 | 7/2010 | Abelyan et al. |
| 2010/0227034 A1 | 9/2010 | Purkayastha et al. |
| 2010/0255171 A1 | 10/2010 | Purkayastha et al. |
| 2010/0278993 A1 | 11/2010 | Prakash et al. |
| 2010/0316782 A1 | 12/2010 | Shi et al. |
| 2011/0030457 A1 | 2/2011 | Valery et al. |
| 2011/0033525 A1 | 2/2011 | Lui |
| 2011/0092684 A1 | 4/2011 | Abelyan et al. |
| 2011/0104353 A1 | 5/2011 | Lee |
| 2011/0111115 A1 | 5/2011 | Shi et al. |
| 2011/0124587 A1 | 5/2011 | Jackson et al. |
| 2011/0160311 A1 | 6/2011 | Prakash et al. |
| 2011/0189360 A1 | 8/2011 | Yoo et al. |
| 2011/0195169 A1 | 8/2011 | Markosyan et al. |
| 2012/0164678 A1 | 6/2012 | Stephanopoulos et al. |
| 2012/0214752 A1 | 8/2012 | Markosyan |
| 2012/0269954 A1* | 10/2012 | Bridges .............. A23L 2/60 426/658 |

FOREIGN PATENT DOCUMENTS

| | | |
|---|---|---|
| CN | 1100727 | 3/1995 |
| CN | 1112565 | 11/1995 |
| CN | 1192447 | 9/1998 |
| CN | 1238341 | 12/1999 |
| CN | 1349997 | 5/2002 |
| CN | 101200480 | 6/2008 |
| JP | 52005800 | 1/1977 |
| JP | 52083731 | 7/1977 |
| JP | 52100500 | 8/1977 |
| JP | 52136200 | 11/1977 |
| JP | 54030199 | 3/1979 |
| JP | 54132599 | 10/1979 |
| JP | 55039731 | 3/1980 |
| JP | 55081567 | 6/1980 |
| JP | 55092400 | 7/1980 |
| JP | 56099768 | 8/1980 |
| JP | 56109568 | 8/1980 |
| JP | 55120770 | 9/1980 |
| JP | 55138372 | 10/1980 |
| JP | 55159770 | 12/1980 |
| JP | 55162953 | 12/1980 |
| JP | 56121453 | 9/1981 |
| JP | 56121454 | 9/1981 |
| JP | 56121455 | 9/1981 |
| JP | 56160962 | 12/1981 |
| JP | 57002656 | 1/1982 |
| JP | 57005663 | 1/1982 |
| JP | 57046998 | 3/1982 |
| JP | 57075992 | 5/1982 |
| JP | 57086264 | 5/1982 |
| JP | 58020170 | 2/1983 |
| JP | 58028246 | 2/1983 |
| JP | 58028247 | 2/1983 |
| JP | 58212759 | 12/1983 |
| JP | 58212760 | 12/1983 |
| JP | 59045848 | 3/1984 |
| JP | 62166861 | 7/1987 |
| JP | 63173531 | 7/1988 |
| JP | 1131191 | 5/1989 |
| JP | 3262458 | 11/1991 |
| JP | 6007108 | 1/1994 |
| JP | 6192283 | 7/1994 |
| JP | 7143860 | 6/1995 |
| JP | 7177862 | 7/1995 |
| JP | 8000214 | 1/1996 |
| JP | 9107913 | 4/1997 |
| JP | 2000236842 | 9/2000 |
| JP | 2002262822 | 9/2002 |
| JP | 2010516764 | 5/2010 |
| KR | 20070067199 | 6/2007 |
| KR | 20080071605 | 8/2008 |
| KR | 20090021386 | 3/2009 |
| RU | 2111969 | 5/1998 |
| RU | 2123267 | 12/1998 |
| RU | 2156083 | 9/2000 |
| RU | 2167544 | 5/2001 |
| RU | 2198548 | 2/2003 |
| WO | 0015049 | 3/2000 |
| WO | WO-0015049 A1 * | 3/2000 ............ A23G 4/14 |
| WO | 2005089483 | 9/2005 |
| WO | 2006072878 | 7/2006 |
| WO | 2006072879 | 7/2006 |
| WO | 2008/091547 A2 | 7/2008 |
| WO | 2008091547 | 7/2008 |
| WO | 2009108680 | 9/2009 |
| WO | 2009137838 | 11/2009 |
| WO | WO-2009137838 A1 * | 11/2009 ............ A23G 3/36 |
| WO | 2010118218 | 10/2010 |
| WO | WO-2010118218 A1 * | 10/2010 ............ A23L 27/36 |
| WO | 2011059954 | 5/2011 |
| WO | 2011153378 | 12/2011 |
| WO | 2012082493 | 6/2012 |
| WO | 2012082677 | 6/2012 |
| WO | 2013022989 | 2/2013 |

OTHER PUBLICATIONS

Crammer, et al., "Sweet glycosides from the Stevia plant", Chemistry in Britain, Oct. 1986, 915-916, 918.

Darise et al., "Enzymic Transglucosylation of Rubusoside and the Structure-Sweetness Relationship of Steviol Bisglycosides," Agric. Biol. Chem. vol. 48(10), 1984, 2483-2488.

Dubois et al., "Diterpenoid Sweeteners. Synthesis and Sensory Evaluation of Stevioside Analogues with Improved Organoleptic Properties," J_ Med. Chem. vol. 28, (1985) 93-98.

Fuh, , "Purification of steviosides by membrane and ion exchange process", Journal of Food Science, vol. 55, No. 5 1990, 1454-1457.

Fukunaga et al., "Enzymic Transglucosylation Products of Stevioside: Separation and Sweetness-evaluation," Agric. Biol. Chem. vol. 53(6) (1989) 1603-1607.

Fullas et al., "Separation of natural product sweetening agents using overpressured layer chromatography," Journal of Chromatography vol. 464 (1989) 213-219.

(56) References Cited

OTHER PUBLICATIONS

Hale, et al., "Amylase of Bacillus Macerans", Cereal Chemistry, vol. 28, No. 1, Jan. 1951, 49-58.
International Search Report and Written Opinion of PCT/US2010/055960.
International Search Report and Written Opinion of PCT/US2011/028028.
International Search Report and Written Opinion of PCT/US2011/033734.
International Search Report and Written Opinion of PCT/US2011/033737.
International Search Report and Written Opinion of PCT/US2011/033912.
International Search Report and Written Opinion of PCT/US2011/035173.
International Search Report and Written Opinion of PCT/US2011/036063, dated Aug. 5, 2011.
International Search Report and Written Opinion of PCT/US2011/047498, dated Dec. 22, 2011.
International Search Report and Written Opinion of PCT/US2011/047499, dated Dec. 22, 2011.
International Search Report and Written Opinion of PCT/US2011/064343.
International Search Report and Written Opinion of PCT/US2012/024585.
International Search Report and Written Opinion of PCT/US2012/024722.
International Search Report and Written Opinion of PCT/US2012/030210.
International Search Report and Written Opinion of PCT/US2012/043294.
International Search Report and Written Opinion of PCT/US2012/051163.
International Search Report and Written Opinion of PCT/US2012/052659.
International Search Report and Written Opinion of PCT/US2012/052665.
International Search Report and Written Opinion of PCT/US2013/030439.
Jaitak, et al., "An Efficient Microwave-assisted Extraction Process of Stevioside and Rebaudioside-A from Stevia Rebaudiana (Bertoni)", Phytochem. Anal. vol. 20 2009, 240-245.
Kennelly, "Sweet and non-sweet constituents of Stevia rebaudiana", Stevia: The genus *Stevia*, Taylor & Francis, 2002, 68-85.
Kinghorn, "Overview", Stevia: The genus *Stevia*, Taylor & Francis, 2002, 1-17.
Kitahata, S. et al., "Production of Rubusoside Derivatives by Transgalactosylation of Various b-Galactosidases", Agric. Biol. Chem., vol. 53, No. 11 1989, 2923-2928.
Kobayashi, et al., "Dulcoside A and B, New diterpene glycosides from Stevia Rebaudiana", Phytochemistry, vol. 16 1977, 1405-1408.
Kochikyan, et al., "Combined Enzymatic Modification of Stevioside and Rebaudioside A", Applied Biochemistry and Microbiology, vol. 42, No. 1, 2006, 31-37.
Kohda, et al., "New sweet diterpene glucosides from Stevia Rebaudiana", Phytochemistry, vol. 15 1976, 981-983.
Kovylyaeva, et al., "Glycosides from Stevia rebaudiana", Chemistry of Natural Compounds, vol. 43, No. 1 2007, 81-85.
Liu, et al., "Study of stevioside preparation by membrane separation process", Desalination, vol. 83 1991, 375-382.
Lobov, S. V. et al., "Enzymic Production of Sweet Stevioside Derivatives: Transglucosylation of Glucosidases", Agric. Biol. Chem., vol. 55, No. 12 1991, 2959-2965.
Montovaneli, et al., "The effect of temperature and flow rate on the clarification of the aqueous Stevia-extract in fixed-bed column with zeolites", Brazilian Journal of Chemical Engineering, vol. 21, No. 3 2004, 449-458.

Moraes, et al., "Clarification of Stevia rebaudiana (Bert.) Bertoni extract adsorption in modified zeolites", Acta Scientiarum, vol. 23, No. 6 2001, 1375-1380.
Ohta et al., "Characterization of Novel Steviol Glycosides from Leaves of Stevia rebaudiana Morita," J_ Appl. Glycosi., vol. 57, 199-209, 2010.
Phillips, K. C., "Stevia: steps in developing a new sweetener", In T.H. Grenby, Editor, Developments in Sweeteners-3, Elsevier 1987, 1-43.
Pol, et al., "Comparison of two different solvents employed for pressurised fluid extraction of stevioside from Stevia rebaudiana: methanol versus water", Anal Bioanal Chem vol. 388 2007, 1847-1857.
Prakash et al., "Development of rebiana, a natural, non-caloric sweetener," Jul. 1, 2008, Food and Chemical Toxology, vol. 46, Is. 7, Sup. 1, p. S75-S82.
Richman et al., "Fuctional genomics uncovers three glucosyltransferases involved in the synthesis of the major sweet glucosides of Stevia rebaudiana," The Plant Journal, vol. 41 (2005) 56-67.
Sakamoto et al., "Application of 13C NMR Spectroscopy to Chemistry of Natural Glycosides: Rebaudioside-C, a New Sweet Diterpene Glycoside of Stevia Rebaudiana", Chem. Pharm. Bull., vol. 25, 1977, 844-846.
Ohtani et al. "Chapter 7. Methods to improve the taste of the sweet principles of Stevia rebaudiana." The Genus *Stevia*, edited by A. Douglas Kinghorn, CRC Press 2001, Taylor and Francis, London and New York, pp. 138-159.
Shi, et al., "Synthesis of bifunctional polymeric adsorbent and its application in purification of Stevia glycosides", Reactive & Functional Polymers, vol. 50 2002, 107-116.
Shibata et al., "Glucosylation of Steviol and Steviol-Glucosides in Extracts from Stevia rebaudiana Bertoni," Plant Physiol. vol. 95, (1991) 152-156.
Starratt, et al., "Rebaudioside F, a diterpene glycoside from Stevia Rebaudiana", Phytochemistry, vol. 59 2002, 367-370.
Sweet Green Fields, LLC, "Notice to the U.S. Food and Drug Administration (FDA) that the use of Rebiana (Rebaudiosid A) derived from Stevia rebaudiana, as a Food Ingredient is Generally Recognized as Safe (GRAS)," Jan. 15, 2009, http:/www.accessdata.fda.gov/scripts/fcn/gras_notices/grn000282.pdf (obtained from the Web on May 8, 2012) entire document esp. p. 22, Table 1.
Tanaka, 0., "Improvement of taste of natural sweeteners", Pure & Appl. Chem., vol. 69, No. 4 1997, 675-683.
Teo, et al., "Validation of green-solvent extraction combined with chromatographic chemical fingerprint to evaluate quality of Stevia rebaudiana Bertoni", J. Sep. Sci, vol. 32 2009, 613-622.
United Nations' Food and Agriculture Organization/Joint Expert Committee on Food Additives (2010) Steviol Glycosides, Compendium of Food Additive Specifications, FAO JECFA Monographs 10, 17-21.
Van der Maarel et al., "Properties and applications of starch-converting enzymes of the a-amylase family," Journal of Biotechnology, vol. 94 (2002) 137-155.
Vasquez, Stimulation of the Gerbil's Gustatory Receptors by Some Potently Sweet Terpenoids, J. Agric. Food Chem., vol. 41, 1305-1310, 1993.
Yamamoto, K. et al., "Effective Production of Glycosyl-steviosides by a-1,6 Transglucosylation of Dextrin Dextranase", Biosci. Biotech. Biochem. vol. 58, No. 9 1994, 1657-1661.
Yoda, et al., "Supercritical fluid extraction from Stevia rebaudiana Bertoni using CO2 and CO2+ water: extraction kinetics and identification of extracted components", Journal of Food Engineering, vol. 57 2003, 125-134.
Zell, et al., "Investigation of Polymorphism in Aspartame and Neotame Using Solid-State NMR Spectroscopy", Tetrahedron, vol. 56, 2000, 6603-6616.
Zhang, et al., "Membrane-based separation scheme for processing sweetener from Stevia leaves", Food Research International, vol. 33 2000, 617-620.

\* cited by examiner

Rebaudioside A

Rebaudioside B

STEVIA COMPOSITION

BACKGROUND OF THE INVENTION

Field of the Invention

The invention relates to a process for producing a highly purified food ingredient from the extract of the *Stevia rebaudiana* Bertoni plant and its use in various food products and beverages.

Description of the Related Art

Sugar alternatives are receiving increasing attention due to the awareness of many diseases associated with the consumption of high-sugar foods and beverages. However, many artificial sweeteners such as dulcin, sodium cyclamate and saccharin have been banned or restricted in some countries due to concerns about their safety. As a result, non-caloric sweeteners of natural origin are becoming increasingly popular. The sweet herb *Stevia rebaudiana* Bertoni produces a number of diterpene glycosides which feature high intensity sweetness and sensory properties superior to those of many other high potency sweeteners.

The above-mentioned sweet glycosides, have a common aglycon, steviol, and differ by the number and type of carbohydrate residues at the C13 and C19 positions. The leaves of *Stevia* are able to accumulate up to 10-20% (on dry weight basis) steviol glycosides. The major glycosides found in *Stevia* leaves are rebaudioside A (2-10%), stevioside (2-10%), and rebaudioside C (1-2%). Other glycosides such as rebaudioside B, D, E, and F, steviolbioside and rubusoside are found at much lower levels (approx. 0-0.2%).

Two major glycosides—stevioside and rebaudioside A (reb A), were extensively studied and characterized in terms of their suitability as commercial high intensity sweeteners. Stability studies in carbonated beverages confirmed their heat and pH stability (Chang S. S., Cook, J. M. (1983) Stability studies of stevioside and rebaudioside A in carbonated beverages. *J. Agric. Food Chem.* 31: 409-412.)

Steviol glycosides differ from each other not only in their molecular structures, but also by their taste properties. Usually stevioside is found to be 110-270 times sweeter than sucrose, rebaudioside A between 150 and 320 times sweeter than sucrose, and rebaudioside C between 40-60 times sweeter than sucrose. Dulcoside A is 30 times sweeter than sucrose. Rebaudioside A has the least astringent, the least bitter, and the least persistent aftertaste, thus possessing the most favorable sensory attributes in major steviol glycosides (Tanaka O. (1987) Improvement of taste of natural sweeteners. *Pure Appl. Chem.* 69:675-683; Phillips K. C. (1989) *Stevia*: steps in developing a new sweetener. In: Grenby T. H, ed. Developments in sweeteners, vol. 3. Elsevier Applied Science, London. 1-43.) The chemical structure of rebaudioside A is shown in FIG. 1.

Methods for the extraction and purification of sweet glycosides from the *Stevia rebaudiana* plant using water or organic solvents are described in, for example, U.S. Pat. Nos. 4,361,697; 4,082,858; 4,892,938; 5,972,120; 5,962,678; 7,838,044 and 7,862,845.

However, even in a highly purified state, steviol glycosides still possess undesirable taste attributes such as bitterness, sweet aftertaste, licorice flavor, etc. One of the main obstacles for the successful commercialization of *stevia* sweeteners are these undesirable taste attributes. It was shown that these flavor notes become more prominent as the concentration of steviol glycosides increases (Prakash I., DuBois G. E., Clos J. F., Wilkens K. L., Fosdick L. E. (2008) Development of rebiana, a natural, non-caloric sweetener. Food Chem. Toxicol., 46, S75-S82.).

Rebaudioside B (CAS No: 58543-17-2), or reb B, also known as stevioside $A_4$ (Kennelly E. J. (2002) Constituents of *Stevia rebaudiana* In *Stevia*: The genus *Stevia*, Kinghorn A. D. (Ed), Taylor & Francis, London, p. 71), is one of the sweet glycosides found in *Stevia rebaudiana*. Sensory evaluations show that reb B was approximately 300-350 times sweeter than sucrose, while for reb A this value was approximately 350-450 (Crammer, B. and Ikan, R. (1986) Sweet glycosides from the *Stevia* plant. Chemistry in Britain 22, 915-916, and 918). The chemical structure of rebaudioside B is shown in FIG. 2.

It was believed that reb B forms from the partial hydrolysis of rebaudioside A during the extraction process (Kobayashi, M., Horikawa, S., Degrandi, I. H., Ueno, J. and Mitsuhashi, H. (1977) Dulcosides A and B, new diterpene glycosides from *Stevia rebaudiana*. Phytochemistry 16, 1405-1408). However, further research has shown that reb B occurs naturally in the leaves of *Stevia rebaudiana* and is currently one of nine steviol glycosides recognized by FAO/JECFA (United Nations' Food and Agriculture Organization/Joint Expert Committee on Food Additives) in calculating total steviol glycosides' content in commercial steviol glycoside preparations (FAO JECFA (2010) Steviol Glycosides, Compendium of Food Additive Specifications, FAO JECFA Monographs 10, 17-21).

Only a few methods are described in literature for preparing reb B.

Kohda et al., (1976) prepared reb B by hydrolysis of reb A with hesperidinase. Reb B was also prepared by alkaline saponification of reb A. The said saponification was conducted in 10% potassium hydroxide-ethanol. The solution was acidified with acetic acid, and extracted with n-butanol. The butanol layer was washed with water and concentrated at low temperature in vacuo. The residue was crystallized from methanol to give reb B. (Kohda, H., Kasai, R., Yamasaki, K., Murakami, K. and Tanaka, O. (1976) New sweet diterpene glucosides from *Stevia rebaudiana*. Phytochemistry 15, 981-983). The described processes might be suitable for laboratory scale preparation of reb B, but are not suitable for any large scale or commercial reb B preparation.

Ahmed et al., used mild alkaline hydrolysis of reb A to prepare reb B. According to the described procedure, reb A was hydrolyzed to reb B by refluxing with 10% aqueous KOH at 100° C. for 1 hr. After neutralization with glacial acetic acid, the precipitated substance was recrystallized twice from methanol (Ahmed M. S., Dobberstein R. H., and Farnsworth N. R. (1980) *Stevia rebaudiana*: I. Use of p-bromophenacyl bromide to enhance ultraviolet detection of water-soluble organic acids (steviolbioside and rebaudioside B) in high-performance liquid chromatographic analysis, J. Chromatogr., 192, 387-393).

The use of methanol as recrystallization media as described in the literature will require its subsequent removal from the product. It is noted that handling of toxic substances such as methanol requires specialized manufacturing installations and, when applied in food processing, sophisticated food safety measures.

It is also noted that no significant work has been conducted to determine the potential of reb B as a sweetener or food ingredient. Moreover, reb B is often viewed as process artifact and unnecessary impurity in commercial steviol glycosides preparations. No significant evaluation of the influence of reb B on the overall taste profile of steviol glycoside preparations has been conducted.

The water solubility of reb B is reported to be about 0.1% (Kinghorn A. D. (2002) Constituents of *Stevia rebaudiana* In *Stevia*: The genus *Stevia*, Kinghorn A. D. (Ed), Taylor & Francis, London, p. 8). In many food processes where highly concentrated ingredients are used, a highly soluble form of reb B will be necessary.

Considering the facts mentioned above, there is a need to evaluate reb B as a sweetener and food ingredient and to develop a simple and efficient process for food grade reb B preparations suitable for food and other applications.

Within the description of this invention we will show that, when applied in specific manner, reb B may impact the taste profile and offer significant advantages for the use of *stevia* sweeteners in various applications.

SUMMARY OF THE INVENTION

The present invention is aimed to overcome the disadvantages of existing *Stevia* sweeteners. The invention describes a process for producing a high purity food ingredient from the extract of the *Stevia rebaudiana* Bertoni plant and use thereof in various food products and beverages as a sweetness and flavor modifier.

The invention, in part, pertains to an ingredient comprising steviol glycosides of *Stevia rebaudiana* Bertoni plant. The steviol glycodsides are selected from the group consisting of stevioside, rebaudioside A (FIG. 1), rebaudioside B (FIG. 2), rebaudioside C, rebaudioside D, rebaudioside E, rebaudioside F, dulcoside A, steviolbioside, rubusoside, as well as other steviol glycosides found in *Stevia rebaudiana* Bertoni plant and mixtures thereof.

The invention, in part, pertains to a process for producing an ingredient containing rebaudioside B, and stevioside, rebaudioside A, rebaudioside C, rebaudioside D, rebaudioside E, rebaudioside F, dulcoside A, steviolbioside, rubusoside, as well as other steviol glycosides found in *Stevia rebaudiana* Bertoni plant and mixtures thereof.

In the invention, rebaudioside A commercialized by PureCircle Sdn. Bhd. (Malaysia), containing, rebaudioside A (about 95-100%), stevioside (about 0-1%), rebaudioside C (about 0-1%), rebaudioside F (about 0-1%), rebaudioside B (about 0.1-0.8%), rebaudioside D (about 0-1%), and other glycosides amounting to total steviol glycosides' content of at least 95%, may be used as a starting material. Alternatively *stevia* extracts with different ratios of steviol glycosides may be used as starting materials.

The starting material is subjected to partial conversion into reb B using a biocatalyst capable of hydrolyzing β-glucosyl ester bonds. The obtained glycoside mixtures can be used "as-is" as well as by recovering reb B from the mixture and using it as a pure ingredient.

The low solubility reb B may be subjected to additional thermal treatment to increase solubility.

The obtained products were applied in various foods and beverages as sweeteners, sweetener enhancers and flavor modifiers, including soft drinks, ice cream, cookies, bread, fruit juices, milk products, baked goods and confectionary products.

It is to be understood that both the foregoing general description and the following detailed description are exemplary and explanatory and are intended to provide further explanation of the invention as claimed.

BRIEF DESCRIPTION OF THE DRAWINGS

The accompanying drawings are included to provide a further understanding of the invention. The drawings illustrate embodiments of the invention and together with the description serve to explain the principles of the embodiments of the invention.

DETAILED DESCRIPTION OF THE INVENTION

Advantages of the present invention will become more apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

Rebaudioside A commercialized by PureCircle Sdn. Bhd. (Malaysia), containing, rebaudioside A (about 95-100%), stevioside (about 0-1%), rebaudioside C (about 0-1%), rebaudioside D (about 0-1%), rebaudioside F (about 0-1%), rebaudioside B (about 0.1-0.8%) and other glycosides amounting to total steviol glycosides' content of at least about 95%, may be used as a starting material. Alternatively *stevia* extracts with different ratios of steviol glycosides may be used as starting materials.

Figure 1:
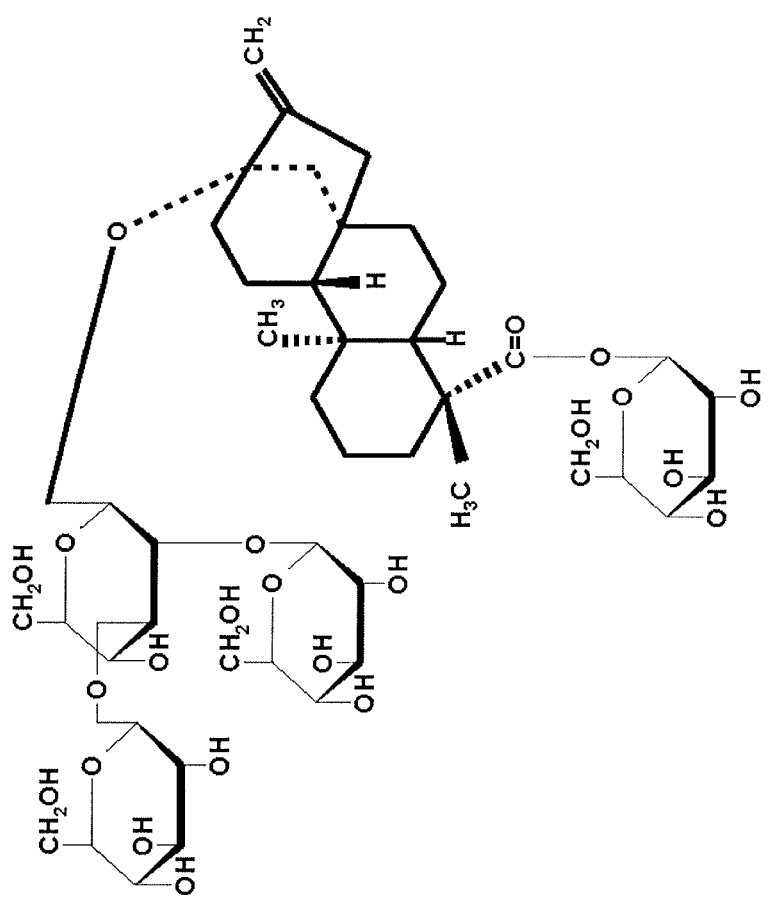
FIG. 1 shows the chemical structure of rebaudioside A.
Figure 2:
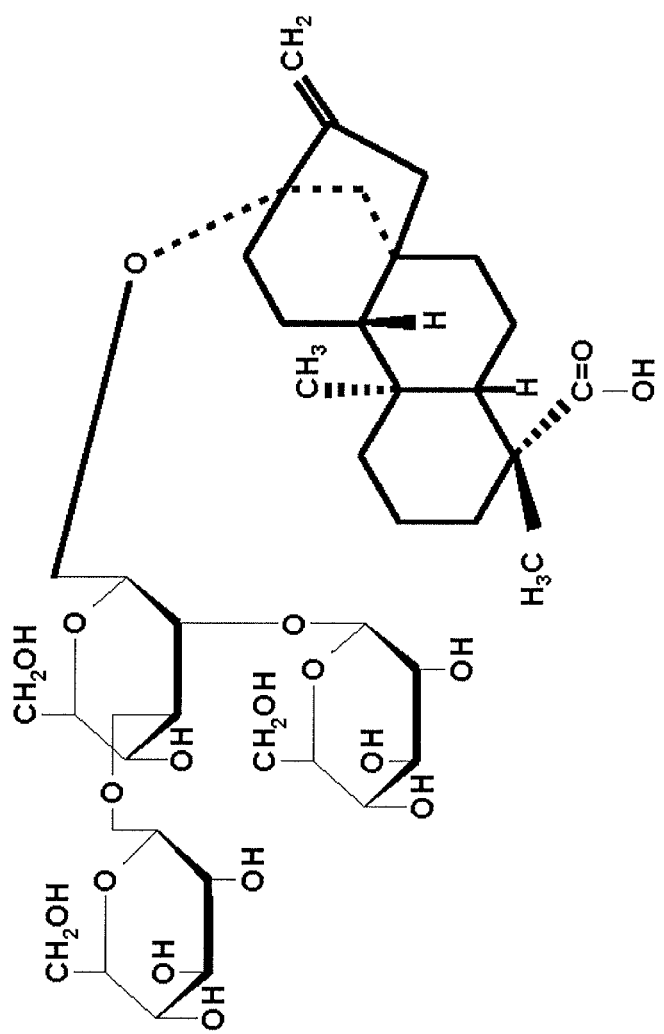
FIG. 2 shows the chemical structure of rebaudioside B
Figure 3:
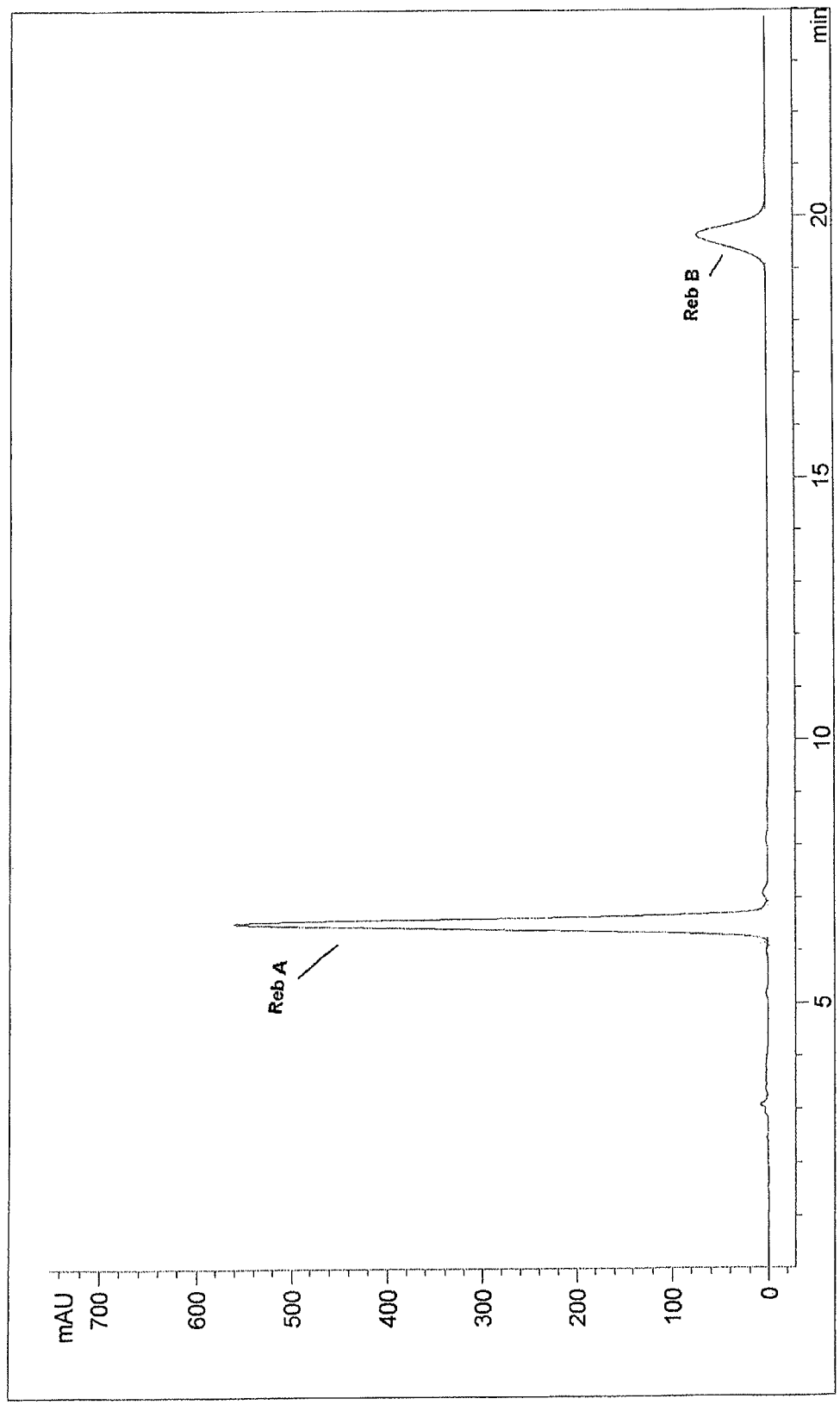
FIG. 3 shows an HPLC chromatogram of a *stevia* composition comprising rebaudioside A and rebaudioside B.

The HPLC analysis of the raw materials and products can be performed on an Agilent Technologies 1200 Series (USA) liquid chromatograph, equipped with Phenomenex Prodigy ODS3, 5 μm (4.6×250 mm) column at 40° C. The mobile phase was 32:68 mixture of acetonitrile and 10 mmol/L sodium phosphate buffer (about pH 2.6) at 1 mL/min. A diode array detector set at 210 nm can be used as the detector. One example of an HPLC chromatogram thus obtained is shown in FIG. 3.

As used herein, unless specified further, "reb B" and "reb B composition" shall be used interchangeably to refer to purified rebaudioside B or rebaudioside B in combination with any other chemical entity.

Preparation of Reb B

1. Biocatalytic Conversion

In one embodiment of the invention, reb A is dispersed in water to form solution. The concentration of reb A is about 0-50% (w/v) preferably about 10-25%. An enzyme preparation selected from group of esterases, lipases, cellulases, hemicellulases, hesperidinases and β-glucosidases, or any enzyme capable of hydrolyzing β-glucosyl ester bonds, or free or immobilized cells, or any other biocatalysts capable of hydrolyzing β-glucosyl ester bonds (the enzyme preparations, enzymes, free or immobilized cells, and other biocatalysts hereinafter collectively referred to as "biocatalysts") are added to reb A solution to form the reaction mixture. The mixture is incubated at about 10-150° C., preferably about 30-100° C., for a period of about 0.5-48 hrs, preferably about 1-24 hrs. As a result reb A is hydrolyzed to reb B. The molar yield of conversion of reb B is about 5-100%, preferably about 10-90%.

After the reaction, the biocatalyst is inactivated by heating or removal from the reaction mixture. The obtained mixture is neutralized by an acid, preferably by sulfuric acid or ortho-phosphoric acid, until a pH of about 3.0-5.0 is reached, preferably until a pH of about 3.0-4.0 is reached. Upon acidification, a precipitate is formed. The precipitate is separated by any method known in the art such as filtration or centrifugation and washed with water until the water reaches a pH of about 4.0-5.0. The obtained crystalline material is dried under vacuum at about 60-105° C. to yield a mixture of reb A and reb B having a ratio of about 5%:95% to about 95%:5% (w/w), preferably about 50%:50% to about 90%:10% (w/w).

2. Optional Post-Conversion Purification

To obtain purified reb B, in one embodiment the separated precipitate described above is suspended in water and the mixture is subjected to continuous agitation over about 0.5-24 hrs, preferably about 1-3 hours, at about 50-100° C., preferably about 60-80° C. The ratio of precipitate to water (w/v) is about 1:5 to about 1:20, preferably about 1:10 to about 1:15. The washed crystals are separated and dried under vacuum at about 60-105° C. to yield reb B with about 99% purity.

3. Optional Post-Conversion Solubility Enhancement

The following procedure can be used to increase the water solubility of reb B or any reb B composition. The obtained compositions generally have a water solubility of less than about 0.2% (w/v). In order to increase the solubility of these compositions, the compositions were combined with the water at ratio of about 1:1 (w/w) and the obtained mixture was further subjected to a gradient heat treatment which resulted in a high stability and high concentration solution. The gradient of about 1° C. per minute was used in heating the mixture. The mixture was heated to the temperature of about 110-140° C., preferably about 118-125° C. and was held at maximum temperature for about 0-120 min, preferably about 50-70 min. After the heat treatment, the solution was cooled down to room temperature at gradient of about 1° C. per minute. The solution was spray dried by a laboratory spray drier operating at about 175° C. inlet and about 100° C. outlet temperatures. An amorphous form of the composition was obtained with greater than about 20% solubility in water at room temperature.

Use of Reb B Compositions

The reb B compositions described above can be used as a sweetness enhancer, a flavor enhancer and/or a sweetener in various food and beverage products. Non-limiting examples of food and beverage products include carbonated soft drinks, ready to drink beverages, energy drinks, isotonic drinks, low-calorie drinks, zero-calorie drinks, sports drinks, teas, fruit and vegetable juices, juice drinks, dairy drinks, yoghurt drinks, alcohol beverages, powdered beverages, bakery products, cookies, biscuits, baking mixes, cereals, confectioneries, candies, toffees, chewing gum, dairy products, flavored milk, yoghurts, flavored yoghurts, cultured milk, soy sauce and other soy base products, salad dressings, mayonnaise, vinegar, frozen-desserts, meat products, fish-meat products, bottled and canned foods, tabletop sweeteners, fruits and vegetables.

Additionally the compositions can be used in drug or pharmaceutical preparations and cosmetics, including but not limited to toothpaste, mouthwash, cough syrup, chewable tablets, lozenges, vitamin preparations, and the like.

The compositions can be used "as-is" or in combination with other sweeteners, flavors and food ingredients.

Non-limiting examples of sweeteners include steviol glycosides, stevioside, rebaudioside A, rebaudioside B, rebaudioside C, rebaudioside D, rebaudioside E, rebaudioside F, dulcoside A, steviolbioside, rubusoside, as well as other steviol glycosides found in *Stevia rebaudiana* Bertoni plant and mixtures thereof, *stevia* extract, Luo Han Guo extract, mogrosides, high-fructose corn syrup, corn syrup, invert sugar, fructooligosaccharides, inulin, inulooligosaccharides, coupling sugar, maltooligosaccharides, maltodextrins, corn syrup solids, glucose, maltose, sucrose, lactose, aspartame, saccharin, sucralose, sugar alcohols.

Non-limiting examples of flavors include lemon, orange, fruit, banana, grape, pear, pineapple, bitter almond, cola, cinnamon, sugar, cotton candy, vanilla flavors.

Non-limiting examples of other food ingredients include flavors, acidulants, organic and amino acids, coloring agents, bulking agents, modified starches, gums, texturizers, preservatives, antioxidants, emulsifiers, stabilisers, thickeners, gelling agents.

The following examples illustrate various embodiments of the invention. It will be understood that the invention is not limited to the materials, proportions, conditions and procedures set forth in the examples, which are only illustrative.

Example 1

Preparation of *Stevia* Composition 1 g of rebaudioside A produced by PureCircle Sdn. Bhd. (Malaysia), containing, 98.1% rebaudioside A, 0.3% stevioside, 0.2 rebaudioside C, 0.2% rebaudioside F, 0.4% rebaudioside B and 0.6% rebaudioside D was dissolved in 10 mL 0.1M phosphate buffer (pH 7.0) and about 1 mg of hesperidinase purchased from Sigma-Aldrich (USA) was added. The mixture was incubated at 37° C. for 24 hours. Then the mixture was boiled at 100° C. for 15 min and filtered through the layer of activated carbon. The filtrate temperature was adjusted to 20° C. and the pH was adjusted to pH 4.0 with ortho-phosphoric acid. The solution was held under moderate agitation conditions for 4 hours and a precipitate was formed. The precipitate was filtered and washed on the filter with 2000 mL of water. The washed crystals were dried under vacuum to yield 0.9 g material containing about 84% reb A and 16% reb B. The water solubility (at 25° C.) of obtained material was about 0.2% (w/v).

Example 2

Preparation of *Stevia* Composition 1 g of rebaudioside A produced by PureCircle Sdn. Bhd. (Malaysia), containing, 98.1% rebaudioside A, 0.3% stevioside, 0.2 rebaudioside C, 0.2% rebaudioside F, 0.4% rebaudioside B and 0.6% rebaudioside D was dissolved in 10 mL 0.1M phosphate buffer (pH 7.0) and about 1 mg of hesperidinase purchased from Sigma-Aldrich (USA) was added. The mixture was incubated at 37° C. for 36 hours. Then the mixture was boiled at 100° C. for 15 min and filtered through the layer of activated carbon. The filtrate temperature was adjusted to 20° C. and the pH was adjusted to pH 4.0 with ortho-phosphoric acid. The solution was held under moderate agitation conditions for 4 hours and a precipitate was formed. The precipitate was filtered and washed on the filter with 2000 mL of water. The washed crystals were dried under vacuum to yield about 0.75 g material containing about 9% reb A and about 91% reb B. The water solubility (at 25° C.) of obtained material was about 0.1% (w/v).

Example 3

Preparation of *Stevia* Composition 1 g of rebaudioside A produced by PureCircle Sdn. Bhd. (Malaysia), containing, 98.1% rebaudioside A, 0.3% stevioside, 0.2 rebaudioside C, 0.2% rebaudioside F, 0.4% rebaudioside B and 0.6% rebaudioside D was dissolved in 10 mL 0.1M phosphate buffer (pH 7.0) and about 1 mg of hesperidinase purchased from Sigma-Aldrich (USA) was added. The mixture was incubated at 37° C. for 48 hours. Then the mixture was boiled at 100° C. for 15 min and filtered through the layer of activated carbon. The filtrate temperature was adjusted to 20° C. and the pH was adjusted to pH 4.0 with ortho-phosphoric acid. The solution was held under moderate agitation conditions for 4 hours and a precipitate was formed. The precipitate was filtered and washed on the filter with 2000 mL of water. The washed crystals were dried under vacuum to yield about 0.7 g material containing about 99.1% reb B. The water solubility (at 25° C.) of obtained material was about 0.1% (w/v).

Example 4

Preparation of Stevia Composition 75 g of material prepared according to EXAMPLE 2 was suspended in 1000 mL water. The mixture temperature was increased to 70° C. The suspension was held under moderate agitation conditions for 4 hours. The crystals were filtered and dried under vacuum to yield about 65 g material containing about 99.0% reb B. The water solubility (at 25° C.) of obtained material was about 0.1% (w/v).

Example 5

Preparation of Soluble Stevia Composition 50 g material prepared according to EXAMPLE 1 was mixed with 50 g of water and incubated in thermostatted oil bath. The temperature was increased at 1° C. per minute to 121° C. The mixture was maintained at 121° C. for 1 hour and then the temperature was decreased to room temperature (25° C.) at 1° C. per minute. The solution was dried using YC-015 laboratory spray drier (Shanghai Pilotech Instrument & Equipment Co. Ltd., China) operating at 175° C. inlet and 100° C. outlet temperature. About 47 g of an amorphous powder was obtained with about 25% (w/v) solubility in water (at 25° C.).

Example 6

Preparation of Soluble Stevia Composition 42 g of reb A produced by PureCircle Sdn. Bhd. (Malaysia) with purity of 99.2% (dry basis) and 8 g of reb B prepared according to EXAMPLE 4 were mixed with 50 g of water and incubated in thermostatted oil bath. The temperature was increased at 1° C. per minute to 121° C. The mixture was maintained at 121° C. for 1 hour and then the temperature was decreased to room temperature (25° C.) at 1° C. per minute. The solution was dried using YC-015 laboratory spray drier (Shanghai Pilotech Instrument & Equipment Co. Ltd., China) operating at 175° C. inlet and 100° C. outlet temperature. About 48 g of an amorphous powder was obtained with about 1.5% (w/v) solubility in water (at 25° C.).

Example 7

Low-Calorie Orange Juice Drink

Orange concentrate (35%), citric acid (0.35%), ascorbic acid (0.05%), orange red color (0.01%), orange flavor (0.20%), and 0.05% stevia composition, were blended and dissolved completely in water (up to 100%) and pasteurized. The stevia composition was selected from a commercial stevia extract (containing stevioside 26%, rebaudioside A 55%, and 16% of other glycosides), a commercial rebaudioside A (containing 98.2% reb A) or material obtained according to EXAMPLE 5.

The sensory evaluations of the samples are summarized in Table 1. The data shows that the best results can be obtained by using the composition obtained according to EXAMPLE 5. Particularly the drinks prepared with said composition exhibited a rounded and complete flavor profile and mouthfeel.

TABLE 1

Evaluation of orange juice drink samples

| Sample | Comments | | |
|---|---|---|---|
| | Flavor | Aftertaste | Mouthfeel |
| Stevia Extract | Sweet, licorice notes | Bitterness and aftertaste | Not acceptable |
| Reb A | Sweet, slight licorice notes | Slight bitterness and aftertaste | Not acceptable |
| EXAMPLE 5 | High quality sweetness, pleasant taste similar to sucrose, rounded and balanced flavor | Clean, no bitterness and no aftertaste | Full |

The same method can be used to prepare juices and juice drinks from other fruits, such as apples, lemons, apricots, cherries, pineapples, mangoes, etc.

Example 8

Zero-Calorie Carbonated Beverage

Carbonated beverages according to the formulas presented in Table 2 were prepared.

TABLE 2

Carbonated Beverage Formulas

| Ingredients | Quantity, % | | |
|---|---|---|---|
| | Stevia Extract | Reb A | EXAMPLE 5 |
| Cola flavor | 0.340 | 0.340 | 0.340 |
| ortho-Phosphoric acid | 0.100 | 0.100 | 0.100 |
| Sodium citrate | 0.310 | 0.310 | 0.310 |
| Sodium benzoate | 0.018 | 0.018 | 0.018 |
| Citric acid | 0.018 | 0.018 | 0.018 |
| Stevia composition | 0.050 | 0.050 | 0.050 |
| Carbonated water | to 100 | to 100 | to 100 |

The sensory properties were evaluated by 20 panelists. The results are summarized in Table 3.

TABLE 3

Evaluation of zero-calorie carbonated beverage samples

| Taste attribute | Number of panelists detected the attribute | | |
|---|---|---|---|
| | Stevia Extract | Reb A | EXAMPLE 5 |
| Bitter taste | 15 | 10 | 0 |
| Astringent taste | 16 | 9 | 0 |

TABLE 3-continued

Evaluation of zero-calorie carbonated beverage samples

| | Number of panelists detected the attribute | | |
|---|---|---|---|
| Taste attribute | Stevia Extract | Reb A | EXAMPLE 5 |
| Aftertaste Comments | 14 | 12 | 0 |
| Quality of sweet taste | Bitter aftertaste (15 of 20) | Bitter aftertaste (10 of 20) | Clean (20 of 20) |
| Overall evaluation | Satisfactory (1 of 20) | Satisfactory (5 of 20) | Satisfactory (20 of 20) |

The above results show that the beverages prepared using the composition obtained according to EXAMPLE 5 possessed the best organoleptic characteristics.

Example 9

Diet Cookies

Flour (50.0%), margarine (30.0%) fructose (10.0%), maltitol (8.0%), whole milk (1.0%), salt (0.2%), baking powder (0.15%), vanillin (0.1%) and different stevia compositions (0.03%) were kneaded well in dough-mixing machine. The obtained dough was molded and baked in oven at 200° C. for 15 minutes. The stevia compositions were selected from a commercial stevia extract (containing stevioside 26%, rebaudioside A 55%, and 16% of other glycosides), a commercial rebaudioside A (containing 98.2% reb A) and material obtained according to EXAMPLE 5.

The sensory properties were evaluated by 20 panelists. The best results were obtained in samples containing the composition obtained according to EXAMPLE 5. The panelists noted a rounded and complete flavor profile and mouthfeel.

Example 10

Yoghurt

Different stevia compositions (0.03%) and sucrose (4%) were dissolved in low fat milk. The stevia compositions were selected from a commercial stevia extract (containing stevioside 26%, rebaudioside A 55%, and 16% of other glycosides), a commercial rebaudioside A (containing 98.2% reb A) and the material obtained according to EXAMPLE 5. After pasteurizing at 82° C. for 20 minutes, the milk was cooled to 37° C. A starter culture (3%) was added and the mixture was incubated at 37° C. for 6 hours then at 5° C. for 12 hours.

The sensory properties were evaluated by 20 panelists. The best results were obtained in samples containing the composition obtained according to EXAMPLE 5. The panelists noted a rounded and complete flavor profile and mouthfeel.

It is to be understood that the foregoing descriptions and specific embodiments shown herein are merely illustrative of the best mode of the invention and the principles thereof, and that modifications and additions may be easily made by those skilled in the art without departing for the spirit and scope of the invention, which is therefore understood to be limited only by the scope of the appended claims.

What is claimed is:

1. A soluble *stevia* composition comprising a gradient heat-treated rebaudioside A and rebaudioside B mixture, wherein the ratio of rebaudioside A and rebaudioside B in the mixture is about 84%:16% (w/w), wherein the gradient heat-treated rebaudioside A and rebaudioside B mixture is provided in an amorphous powder form, and wherein the composition has a solubility of greater than about 20% in water at room temperature.

2. A sweetener comprising the *stevia* composition of claim 1 and an additional sweetening agent selected from the group consisting of: *stevia* extract, steviol glycosides, stevioside, rebaudioside C, rebaudioside D, rebaudioside E, rebaudioside F, dulcoside A, steviolbioside, rubusoside, other steviol glycosides found in *Stevia rebaudiana* Bertoni plant and mixtures thereof, Luo Han Guo extract, mogrosides, high-fructose corn syrup, corn syrup, invert sugar, fructooligosaccharides, inulin, inulooligosaccharides, coupling sugar, maltooligosaccharides, maltodextrins, corn syrup solids, glucose, maltose, sucrose, lactose, aspartame, saccharin, sucralose, sugar alcohols, and a combination thereof.

3. A flavor comprising the *stevia* composition of claim 1 and a flavoring agent selected from the group consisting of: lemon, orange, fruit, banana, grape, pear, pineapple, mango, bitter almond, cola, cinnamon, sugar, cotton candy, vanilla, and a combination thereof.

4. A food ingredient comprising the *stevia* composition of claim 1 and a food ingredient selected from the group consisting of: acidulants, organic and amino acids, coloring agents, bulking agents, modified starches, gums, texturizers, preservatives, antioxidants, emulsifiers, stabilisers, thickeners, gelling agents, and a combination thereof.

5. A food, beverage, pharmaceutical or cosmetic composition comprising the *stevia* composition of claim 1.

6. The *stevia* composition of claim 1, wherein the *stevia* composition has a solubility of about 25% in water at 25° C.

7. The *stevia* composition of claim 1, wherein the *stevia* composition is completely soluble in acidified water.

* * * * *